US00PP33903P2

(12) United States Plant Patent
Snijder

(10) Patent No.: US PP33,903 P2
(45) Date of Patent: Jan. 25, 2022

(54) *VERBENA* PLANT NAMED 'VEAZ0067'

(50) Latin Name: *Verbena hybrida*
Varietal Denomination: VEAZ0067

(71) Applicant: SYNGENTA CROP PROTECTION AG, Basel (CH)

(72) Inventor: Ronald Christiaan Snijder, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/360,434

(22) Filed: Jun. 28, 2021

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
CPC ..... A01H 6/86
See application file for complete search history.

(56) References Cited

PUBLICATIONS

CPVO hit on a *Verbena* plant named, 'VEAZ0067', https://cpvo.europa.eu/en/applications-and-examinations/official-publications accessed Sep. 10, 2021.*
UPOV hit on *Verbena* plant named, 'VEAZ0067', QZ PBR 2021/1704, filed Jun. 24, 2021.*

* cited by examiner

*Primary Examiner* — Anne Marie Grunberg
(74) *Attorney, Agent, or Firm* — Dale Skalla

(57) ABSTRACT

A new *Verbena* plant named 'VEAZ0067' particularly distinguished with medium sized inflorescences, bicolored flowers of medium size, with red upper petals and densely pink-red mottled lower petals, medium green toothed leaves, and a semi-trailing plant habit.

1 Drawing Sheet

Latin name of the genus and species of the plant claimed: *Verbena hybrida.*
Varietal denomination: 'VEAZ0067'.

BACKGROUND OF THE NEW PLANT

The present invention comprises a new *Verbena*, botanically known as *Verbena hybrida*, and hereinafter referred to by the variety name 'VEAZ0067'.

'VEAZ0067' is a product of a planned breeding program. The new cultivar has medium sized inflorescences, bicolored flowers of medium size, with red upper petals and densely pink-red mottled lower petals, medium green toothed leaves, and a semi-trailing plant habit.

'VEAZ0067' originated from a cross made in September 2017 in the greenhouse in Enkhuizen, The Netherlands.

The female parent was a patented plant 'KLEVP15474', (U.S. Plant Pat. No. 28,454) having a more orange red type of flower color. The male parent was an unpatented proprietary plant designated 'T0984-4V', with duller red colored flowers.

The resulting seed was sown in February 2018 in a greenhouse in Enkhuizen, The Netherlands, and 'VEAZ0067' was selected as one flowering plant within the progeny of the stated cross in May 2018.

The first act of asexual reproduction of 'VEAZ0067' was accomplished when vegetative cuttings were propagated from the initial selection in June 2018 in a greenhouse in Enkhuizen, The Netherlands.

BRIEF SUMMARY OF INVENTION

Horticultural examination of plants grown from cuttings of the plant initiated in the fall of 2018, and continuing thereafter, has demonstrated that the combination of characteristics as herein disclosed for 'VEAZ0067' are firmly fixed and are retained through successive generations of asexual reproduction.

'VEAZ0067' has not been observed under all possible environmental conditions. The phenotype may vary significantly with variations in environment such as temperature, light intensity, and day length.

A Plant Breeder's Right for this cultivar has not yet been applied for. 'VEAZ0067' has not been made publicly available prior to the effective filing date of this application, notwithstanding any disclosure that may have been made less than one year prior to the effective filing date of this application by the inventor or another who obtained 'VEAZ0067' directly from the inventor.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

Figure 1:
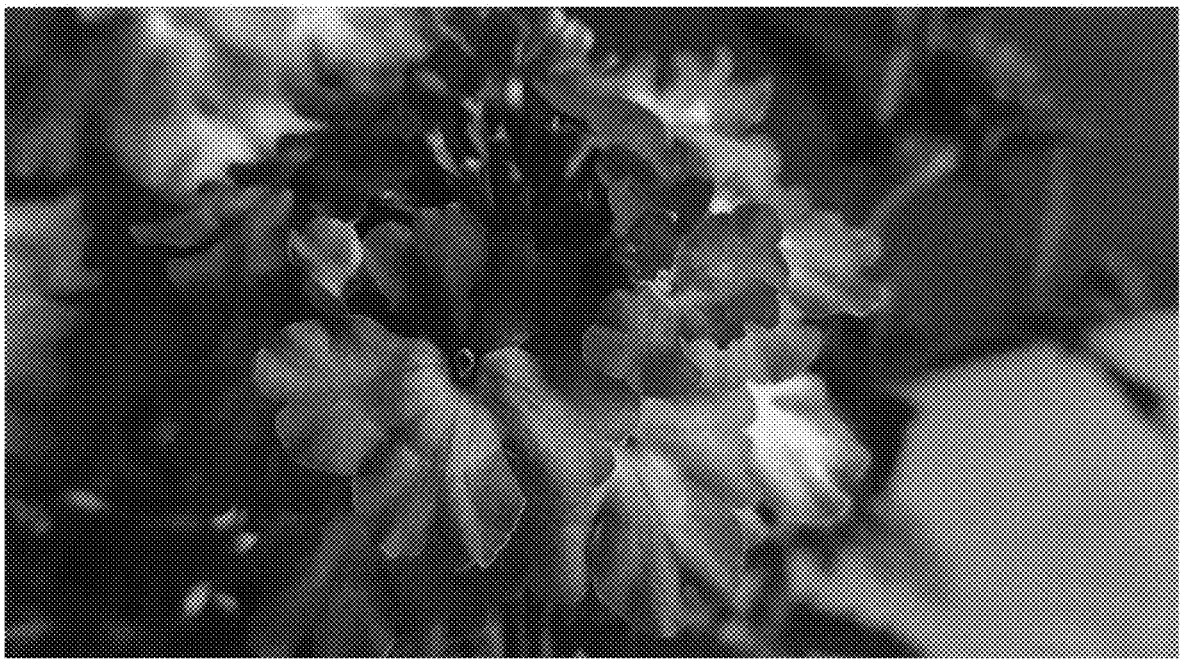
Figure 2:
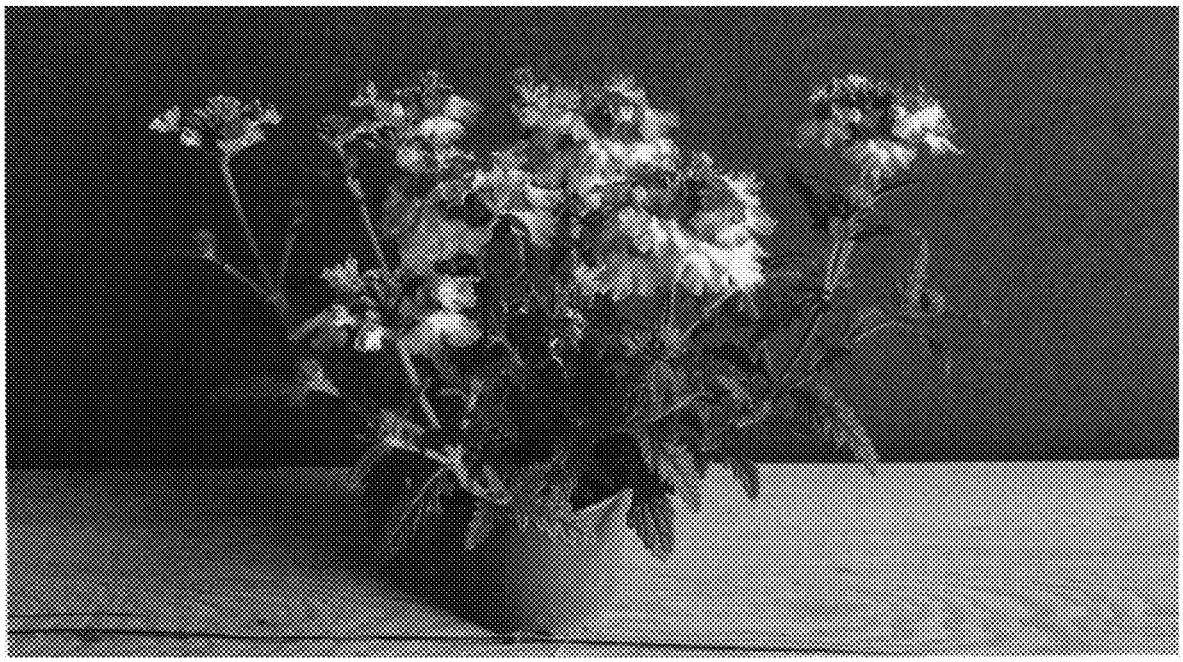

The accompanying photographic drawings show typical flower and foliage characteristics of 'VEAZ0067' with colors being as true as possible with an illustration of this type. The photographic drawing in FIG. 1 shows a close view of an inflorescence of the new plant, and in FIG. 2 a whole flowering plant.

The aforementioned photographs were taken in June 2021 in Andijk, The Netherlands. The plants were about 10 week old and were grown in 11 cm pots.

DETAILED BOTANICAL DESCRIPTION

Colour references are made to The Royal Horticultural Society Colour Chart 2001.

TABLE 1

DIFFERENCES BETWEEN THE NEW VARIETY 'VEAZ0067' AND A MOST SIMILAR VARIETY

| | 'VEAZ0067' | 'VEAZ0057' (U.S. Plant Pat. No. 32,635) |
|---|---|---|
| Flower color: | Lower 3 petals pink color around corolla tube at anthesis | Lower 3 petals with white center around corolla tube at anthesis |
| Bud color: | Pink, RHS 62C | White, RHS N155A |
| Color lower surface of lower petal: | Pink, RHS 69D | White, RHS N155A |

Plant:

*Form, growth and habit.*—Herbaceous, initially upright, then outwardly spreading; vigorous and free-branching.

*Plant height.*—15 cm.

*Plant height (inflorescence included).*—19 cm.

*Plant width.*—25 cm.

Roots:

*Number of days to initiate and produce roots.*—11-14 days at about 22 degrees C.

*Type.*—Fine, fibrous, free branching.

*Color.*—RHS N155B but whiter.

Foliage:

*Arrangement.*—Opposite, simple.

*Immature, leaf color, upper surface.*—RHS 137A.

*Immature, leaf color, lower surface.*—RHS 137D.

*Mature, leaf color, upper surface.*—RHS 137B.

*Mature, leaf color, lower surface.*—RHS 138B.

*Length.*—4.5-5 cm.

*Width.*—2-2.5 cm.

*Shape.*—Lanceolate.

*Base shape.*—Decurrent.

*Apex shape.*—Acute.

*Margin.*—Dentate.

*Texture, upper surface.*—Hirsute.

*Texture, lower surface.*—Hirsute.

*Color of veins, upper surface.*—Indistinct, RHS 137A.

*Color of veins, lower surface.*—RHS 138D.

*Pattern of veining.*—Pinnate.

*Petiole color.*—RHS 144D.

*Petiole length.*—0-0.2 cm.

*Petiole width.*—0.2-0.3 cm.

*Texture.*—Hirsute.

Stem:

*Branching characteristics.*—Makes branches on every node.

*Quantity of main branches per plant.*—6-12.

*Color of stem.*—RHS 138B.

*Stem length.*—15-20 cm.

*Stem width.*—About 0.3 cm.

*Length of internodes.*—2-5 cm.

*Texture.*—Hirsute.

*Color of peduncle.*—RHS 138B.

*Length of peduncle.*—2.5-3.5 cm.

*Peduncle diameter.*—0.2 cm.

*Texture.*—Canescent.

Inflorescence:

*Type.*—Umbel-like, but actually a spike, umbrella-shaped, large.

*Blooming habit.*—Flowers continuously through the summer months.

*Lastingness of individual blooms on the plant.*—About 8 days in the greenhouse.

*Number of inflorescences per plant.*—25 to 35 at various stages.

*Horizontal diameter of inflorescence.*—About 6 cm.

*Depth of inflorescence.*—3-4 cm.

*Number of florets per inflorescence (including any buds at the time).*—34-40.

Bud (just when opening/showing color):

*Color.*—RHS 62C.

*Length.*—1 cm.

*Width.*—0.6 cm.

*Shape.*—Tubular with a bulbous end.

Floret:

*Form.*—Sessile; salver-shape, composed of 5 partly fused petals with a base of a narrow tube.

*Immature color, upper surface.*—upper petal RHS 46A fading to RHS 46D at the edge; lower petal RHS 69A, densely mottled RHS 63B.

*Immature color, lower surface.*—upper petal RHS 55C, densely mottled RHS 54A; lower petal RHS 56D.

*Mature color, upper surface.*—Upper petal RHS 53C, lower petal RHS 69D, towards edge increasingly mottled RHS 58B.

*Mature color, lower surface.*—Upper petal RHS 69D, mottled RHS 63C; lower petal RHS 69D fading to RHS N77D at the base.

*Floret diameter.*—2.5 cm.

*Floret length (depth).*—0.2 cm.

*Number of petals.*—Gamopetalous, 5 lobed.

*Petal length.*—Upper petal 0.8 cm; lower petal 1.1 cm.

*Petal width.*—Upper petal 0.7cm; lower petal 0.9 cm.

*Shape.*—Obcordate.

*Apex shape.*—Emarginate.

*Margin.*—Entire.

*Petal texture, upper surface.*—Smooth.

*Petal texture, lower surface.*—Papillose.

*Corolla tube length.*—1.9 cm.

*Corolla tube width.*—0.1 cm at base, tapering to 0.3 cm at corolla tube opening.

*Corolla tube color inside.*—RHS 157B.

*Tube color outside.*—RHS 157B.

*Corolla texture, inside.*—Papillose.

*Corolla texture, outside.*—Glabrous.

*Throat hair color.*—RHS 155A.

Calyx:

*Type.*—Five sepals whose margins are fused to each other along their length, with a transparent membrane of less than 0.1 cm in width and with one smaller sepal attached to the base of the calyx.

*Color of sepals.*—RHS 138B, striped RHS 138A.

*Length of sepals.*—1.3 cm.

*Width of sepals.*—0.25 cm.

*Sepal shape.*—Linear, but fused.

*Apex shape.*—Acute.

*Margins.*—Entire.

*Texture.*—Densely covered with short hair.

Reproductive organs:

Gynoecium:

*Pistil.*—1.

*Pistil length.*—1.3 cm.

*Style color.*—RHS 144D.

*Style length.*—1.7 cm.

*Stigma color.*—RHS 144A.

*Ovary color.*—RHS 144B.

*Ovary length.*—0.22 cm.

*Ovary width.*—0.1 cm.

Androecium:

*Stamens.*—Anthers and filaments fused to upper half of corolla tube; four anthers with two pollen sacs per anther.

*Color of filaments.*—RHS 157D.

*Filament length.*—0.25 cm.

*Anther color.*—RHS 151C.

*Anther length.*—0.1 cm.

*Pollen amount.*—Scarce.

Fertility/seed set: Neither seed nor fruit production has been observed.

Disease/pest resistance: Resistance to pathogens and pests common to *Verbena* has not been observed.

What is claimed is:

1. A new and distinct variety of *Verbena* plant named 'VEAZ0067' substantially as illustrated and described herein.

* * * * *